(12) United States Patent
Chang et al.

(10) Patent No.: US 11,661,946 B2
(45) Date of Patent: May 30, 2023

(54) CEILING FAN AND SURROUNDING DEVICE THEREOF

(71) Applicant: HOTECK INC., Taichung (TW)

(72) Inventors: Chia-Wei Chang, Taichung (TW);
Kai-Jen Tsai, Taichung (TW);
Meng-Yuan Lee, Taichung (TW);
Chung-Yu Lin, Taichung (TW);
Min-Yuan Hsiao, Taichung (TW)

(73) Assignee: HOTECK INC., Taichung (TW)

( * ) Notice: Subject to any disclaimer, the term of this patent is extended or adjusted under 35 U.S.C. 154(b) by 0 days.

(21) Appl. No.: 17/569,730

(22) Filed: Jan. 6, 2022

(65) Prior Publication Data

US 2023/0097560 A1 Mar. 30, 2023

(30) Foreign Application Priority Data

Sep. 24, 2021 (TW) ................. 110211221

(51) Int. Cl.
| F04D 25/08 | (2006.01) |
| A61L 9/20 | (2006.01) |
| F04D 29/04 | (2006.01) |
| F04D 29/043 | (2006.01) |

(52) U.S. Cl.
CPC ............. *F04D 25/088* (2013.01); *A61L 9/20* (2013.01); *F04D 29/043* (2013.01); *F04D 29/0405* (2013.01)

(58) Field of Classification Search
CPC .. F04D 25/088; F04D 29/0405; F04D 29/043; A61L 9/20

USPC ....................................... 416/204 R
See application file for complete search history.

(56) References Cited

U.S. PATENT DOCUMENTS

| 2,354,817 | A | * | 8/1944 | Law | ........................ | A61N 5/06 250/435 |
| 4,422,824 | A | * | 12/1983 | Eisenhardt, Jr. | ...... | F04D 25/088 55/467 |
| 5,847,514 | A | * | 12/1998 | Dai | ........................ | H01T 23/00 315/111.91 |
| 5,887,785 | A | * | 3/1999 | Yilmaz | ................. | F04D 25/166 55/467 |
| 7,115,158 | B1 | * | 10/2006 | Landrum | ................ | B03C 3/383 55/471 |
| 7,201,489 | B2 | * | 4/2007 | Shyu | ................... | F21V 33/0096 362/147 |

(Continued)

*Primary Examiner* — Logan M Kraft
*Assistant Examiner* — John D Bailey
(74) *Attorney, Agent, or Firm* — Li & Cai Intellectual Property (USA) Office

(57) ABSTRACT

A ceiling fan and a surrounding device thereof are provided. The ceiling fan includes a main body, a bracket set connected to the main body, and a surrounding device connected to the bracket set. The main body includes a main shaft, a motor, and a plurality of ceiling fan blades. The bracket set includes a plurality of brackets, and each of the brackets has one end connected to the main shaft. The surrounding device is connected to another end of each of the brackets that is relatively far away from the main shaft, and the surrounding device is roundly arranged around and spaced apart from an end of each of the ceiling fan blades that is relatively far away from the motor. The surrounding device includes at least one functional component that is configured to disinfect or sterilize air or to provide lighting.

9 Claims, 7 Drawing Sheets

(56) References Cited

U.S. PATENT DOCUMENTS

| | | | | |
|---|---|---|---|---|
| 7,318,858 | B2* | 1/2008 | Parsa | B01D 53/323 96/60 |
| 7,674,305 | B2* | 3/2010 | Lillquist | B01D 45/14 55/467 |
| 7,717,674 | B2* | 5/2010 | Tsuji | F04D 25/088 416/247 R |
| 7,763,212 | B2* | 7/2010 | McEllen | F21S 8/04 422/121 |
| 7,879,299 | B2* | 2/2011 | McEllen | A61L 9/18 422/305 |
| 8,080,203 | B2* | 12/2011 | First | A61L 9/20 422/24 |
| 8,100,649 | B2* | 1/2012 | Okimura | F21V 33/0096 416/146 R |
| 8,894,478 | B1* | 11/2014 | Stillwagon | F24F 1/0071 454/231 |
| 9,393,338 | B2* | 7/2016 | Livchak | F28F 1/12 |
| 9,399,998 | B1* | 7/2016 | Hardie | F04D 29/388 |
| 9,402,931 | B2* | 8/2016 | Engelhard | A61L 9/205 |
| 10,125,971 | B2* | 11/2018 | Graziano | F21V 33/0096 |
| 10,449,265 | B2* | 10/2019 | Engelhard | B01D 53/864 |
| 10,987,440 | B1* | 4/2021 | Sood | H05B 47/115 |
| 11,027,038 | B1* | 6/2021 | Rhoades | A61L 9/22 |
| 11,293,458 | B2* | 4/2022 | Jackson | F21V 33/0096 |
| 11,305,031 | B2* | 4/2022 | Sood | A61L 9/22 |
| 11,400,177 | B2* | 8/2022 | Wald | F04D 25/088 |
| 2003/0039577 | A1* | 2/2003 | Nelson | A61L 9/20 422/4 |
| 2005/0058584 | A1* | 3/2005 | Shyu | A61L 9/20 422/4 |
| 2008/0107528 | A1* | 5/2008 | Tsuji | F04D 25/088 416/244 R |
| 2008/0193294 | A1* | 8/2008 | Grant | F24F 7/007 416/204 R |
| 2008/0213094 | A1* | 9/2008 | Okimura | F04D 25/088 416/5 |
| 2009/0035177 | A1* | 2/2009 | McEllen | A61L 9/18 422/4 |
| 2009/0117000 | A1* | 5/2009 | First | A61L 9/20 422/24 |
| 2009/0129974 | A1* | 5/2009 | McEllen | A61L 9/205 422/108 |
| 2009/0208333 | A1* | 8/2009 | Smith | F04D 25/088 416/61 |
| 2013/0101416 | A1* | 4/2013 | Todd | F04D 25/088 416/5 |
| 2013/0114245 | A1* | 5/2013 | Todd, Jr. | F04D 25/088 362/96 |
| 2015/0300368 | A1* | 10/2015 | Hsu | F04D 17/16 415/108 |
| 2017/0248148 | A1* | 8/2017 | Kohen | F24H 3/0411 |
| 2017/0284405 | A1* | 10/2017 | Eggers | F04D 25/088 |
| 2019/0113041 | A1* | 4/2019 | Walker, Jr. | F04D 29/601 |
| 2019/0292315 | A1* | 9/2019 | Niemiec | C08G 81/00 |
| 2019/0383295 | A1* | 12/2019 | Eggers | F04D 29/601 |
| 2020/0354513 | A1* | 11/2020 | Niemiec | E04B 9/02 |
| 2021/0231129 | A1* | 7/2021 | Mason | F04D 25/068 |
| 2021/0293246 | A1* | 9/2021 | Hsieh | F24F 7/007 |
| 2021/0353813 | A1* | 11/2021 | Wald | F04D 25/088 |
| 2021/0353820 | A1* | 11/2021 | Lesser | A61L 9/205 |
| 2021/0355948 | A1* | 11/2021 | Harper | F04D 29/703 |
| 2022/0008596 | A1* | 1/2022 | Sood | A61L 9/20 |
| 2022/0008602 | A1* | 1/2022 | Sood | A61L 2/10 |
| 2022/0133941 | A1* | 5/2022 | Thomsen | F04D 25/088 422/121 |

\* cited by examiner

CEILING FAN AND SURROUNDING DEVICE THEREOF

CROSS-REFERENCE TO RELATED PATENT APPLICATION

This application claims the benefit of priority to Taiwan Patent Application No. 110211221, filed on Sep. 24, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a ceiling fan and a surrounding device thereof, and more particularly to a ceiling fan and a surrounding device thereof that are configured to disinfect or sterilize air or to provide lighting.

BACKGROUND OF THE DISCLOSURE

Usually, a conventional ceiling fan is further installed with a sterilization device (such as an ultraviolet lamp) at a position of a ceiling fan mounting seat thereof, so that the ceiling fan has effects of air filtration and sterilization.

However, since the sterilization device is located close to the ceiling fan mounting seat, only part of the airflow driven by the ceiling fan can pass through the sterilization device. Accordingly, the effects of air filtration and sterilization of the ceiling fan equipped with the sterilization device are limited.

Therefore, how to overcome the above-mentioned deficiency through an improvement in structural design has become one of the important issues to be solved in the related art.

SUMMARY OF THE DISCLOSURE

In response to the above-referenced technical inadequacy, the present disclosure provides a ceiling fan and a surrounding device thereof, so as to effectively overcome issues associated with conventional ceiling fans.

In one aspect, the present disclosure provides a ceiling fan, and the ceiling fan includes a main body, a bracket set, and a surrounding device. The main body includes a main shaft, a motor connected to the main shaft, and a plurality of ceiling fan blades connected to the motor. The bracket set includes a plurality of brackets, and each of the brackets has one end connected to the main shaft. The surrounding device is connected to another end of each of the brackets, and another end of each of the brackets is relatively far away from the main shaft. The surrounding device is roundly arranged around and spaced apart from an end of each of the ceiling fan blades, and the end of each of the ceiling fan blades is distant from the motor. The surrounding device includes at least one functional component configured to disinfect or sterilize air or to provide lighting.

In another aspect, the present disclosure provides a surrounding device that is configured to be roundly arranged around and spaced apart from an end of each of a plurality of ceiling fan blades of a ceiling fan, and the surrounding device includes a surrounding main body and at least one functional component. The surrounding main body includes a plurality of surrounding portions, and the surrounding portions are configured to assemble to each other to correspondingly form the surrounding device in an annular shape. The at least one functional component is disposed on an inside of the surrounding main body, and the at least one functional component is configured to disinfect or sterilize air or to provide lighting.

Therefore, in the ceiling fan and the surrounding device thereof provided by the present disclosure, by virtue of "the surrounding device including the at least one functional component configured to disinfect or sterilize air or to provide lighting" the ceiling fan can be used to disinfect or sterilize the air or to provide lighting.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
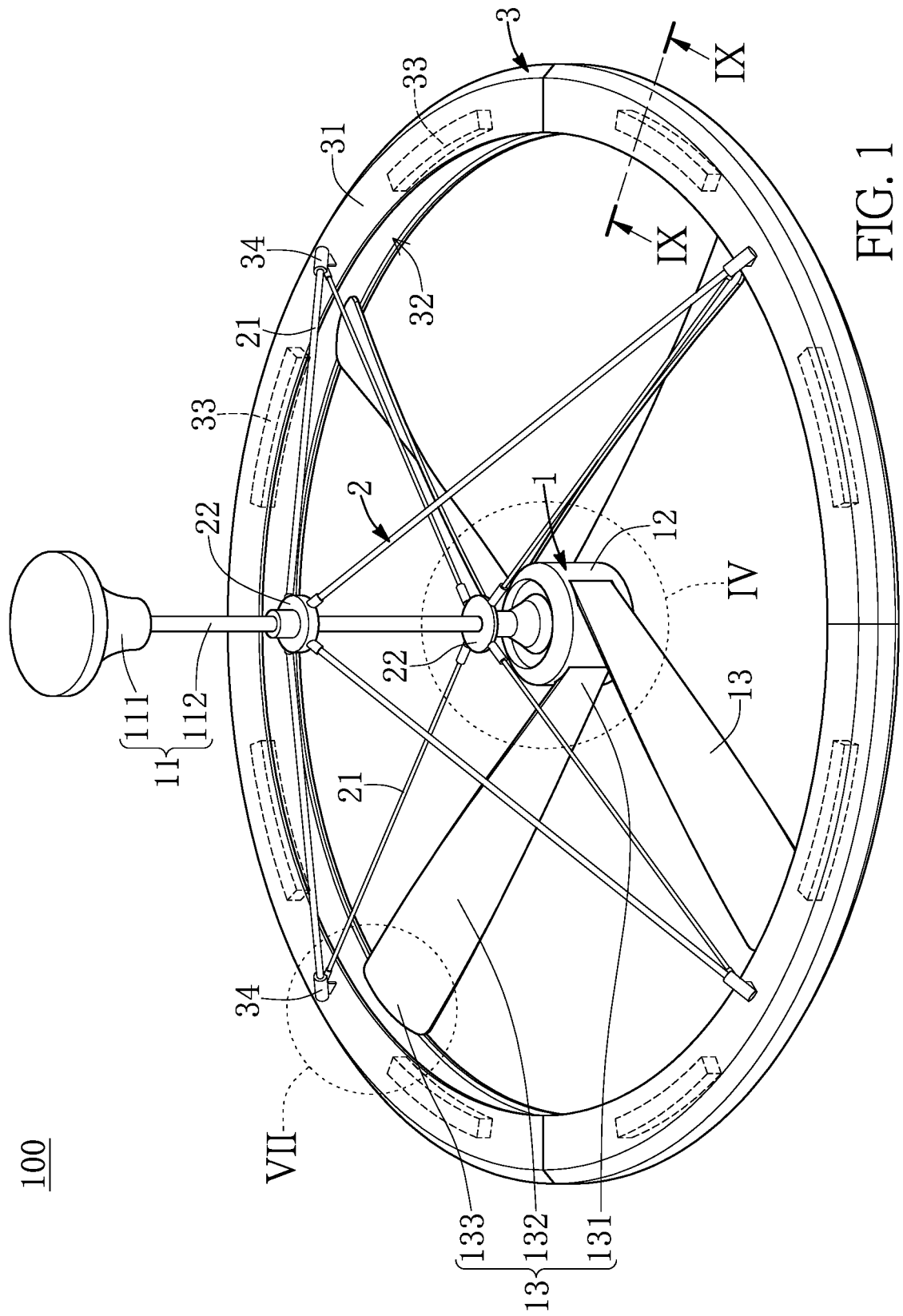
FIG. 1 is a schematic perspective view of a ceiling fan according to an embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
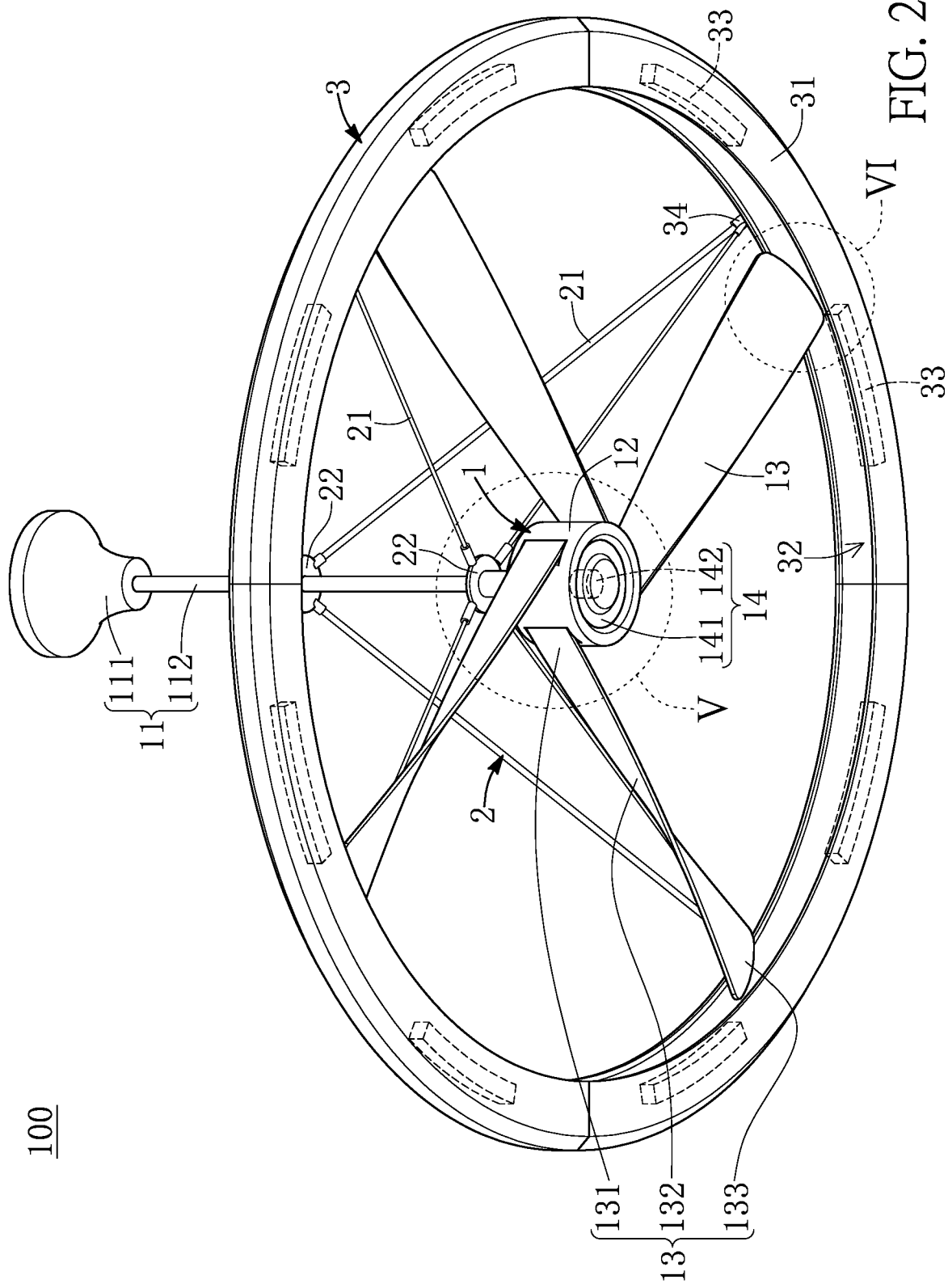
FIG. 2 is another schematic perspective view of the ceiling fan according to the embodiment of the present disclosure.
Figure 3:
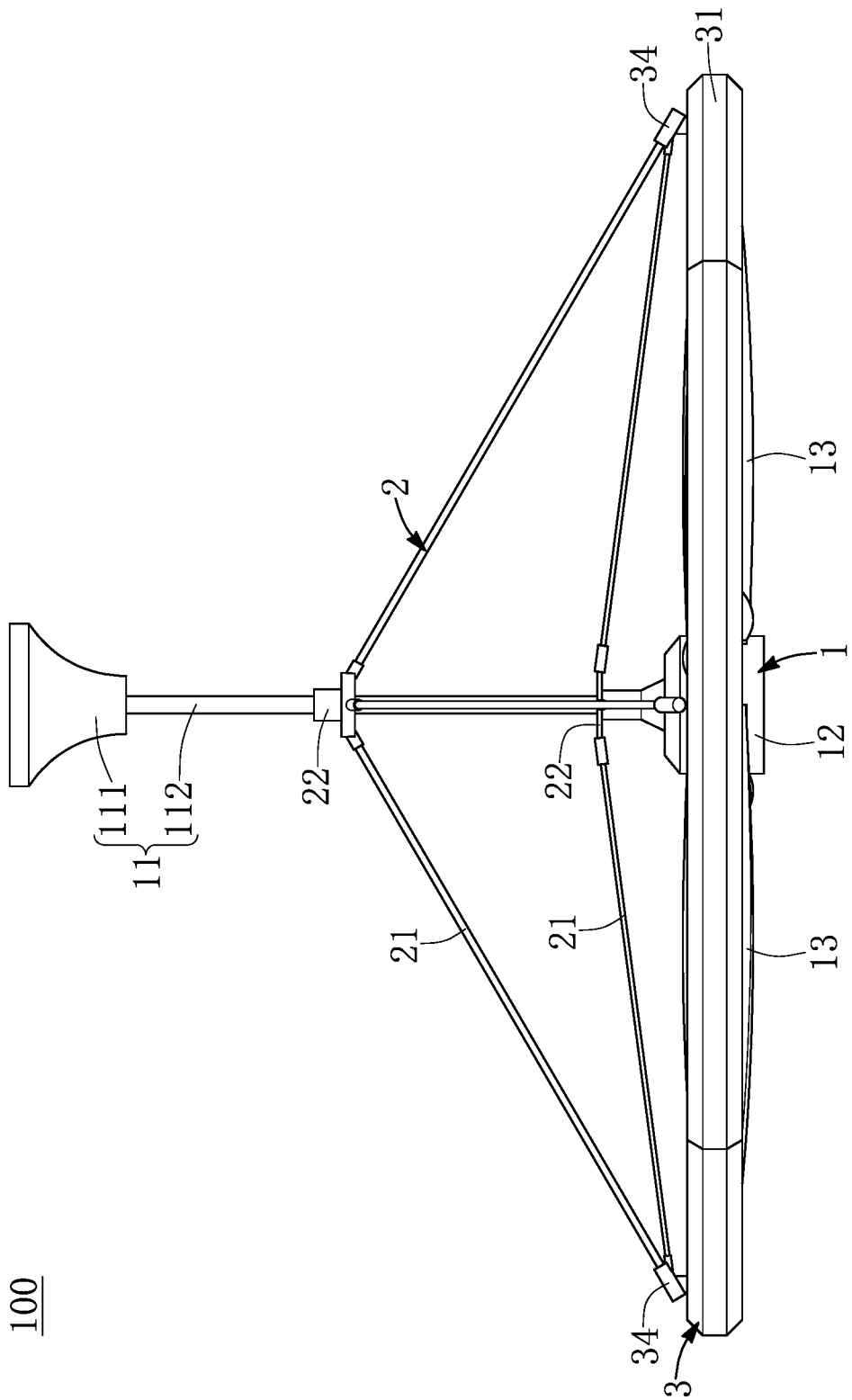
FIG. 3 is a schematic side view of the ceiling fan according to the embodiment of the present disclosure.

Referring to FIG. 1 to FIG. 3, an embodiment of the present disclosure provides a ceiling fan 100 that includes a main body 1, a bracket set 2, and a surrounding device 3. The bracket set 2 is connected to the main body 1, and the surrounding device 3 is connected to the bracket set 2.

In the present embodiment, the surrounding device 3 is described together with the above-mentioned main body 1 and bracket set 2. However, in other embodiments not shown in the present disclosure, the surrounding device 3 can also be independently used (e.g., sold) or used in cooperation with other components. In other words, the surrounding device 3 can also be applied or used in conjunction with only a part of the main body 1 and the bracket set 2.

It should be noted that for ease of illustration, the main body 1, the bracket set 2, and the surrounding device 3 are sequentially described. The connection relationships of the main body 1, the bracket group 2, and the surrounding device 3 will be described in due course.

As shown in FIG. 1 and FIG. 2, the main body 1 includes a main shaft 11, a motor 12, a plurality of ceiling fan blades 13, and a ceiling fan lamp 14. The main shaft 11 has an end connected to the motor 12, the ceiling fan blades 13 are connected to the motor 12, and the ceiling fan lamp 14 is disposed on a side of the motor 12 that is relatively far away from the main shaft 11, but the present disclosure is not limited thereto. For instance, in other embodiments not shown in the present disclosure, the main body 1 can be provided without the ceiling fan lamp 14.

Specifically, the main shaft 11 includes a mounting base 111 and a connecting shaft 112 connected to the mounting base 111, the connecting shaft 112 has an end connected to the mounting base 111, and the connecting shaft 112 has another end connected to the motor 12.

In the present embodiment, the mounting base 111 is mounted on a ceiling of an interior space, the connecting shaft 112 is hollow and is configured to accommodate a plurality of power supply lines (not shown), and the power supply lines are connected to the motor 12 and the ceiling fan lamp 14. It should be noted that a structural improvement of the main shaft 11 is not the focus of the present disclosure, and will not be further described herein.

The motor 12 is a brushless DC motor in the present embodiment, and the motor 12 includes a motor housing (not labeled), a stator (not shown) disposed in the motor housing, and a rotor (not shown) disposed in the motor housing, but the present disclosure is not limited thereto. For instance, the motor 12 can be an AC motor or a brush DC motor in other embodiments of the present disclosure. It should be noted that a structural improvement of the motor 12 is not the focus of the present disclosure, and will not be further described herein.

Figure 4:
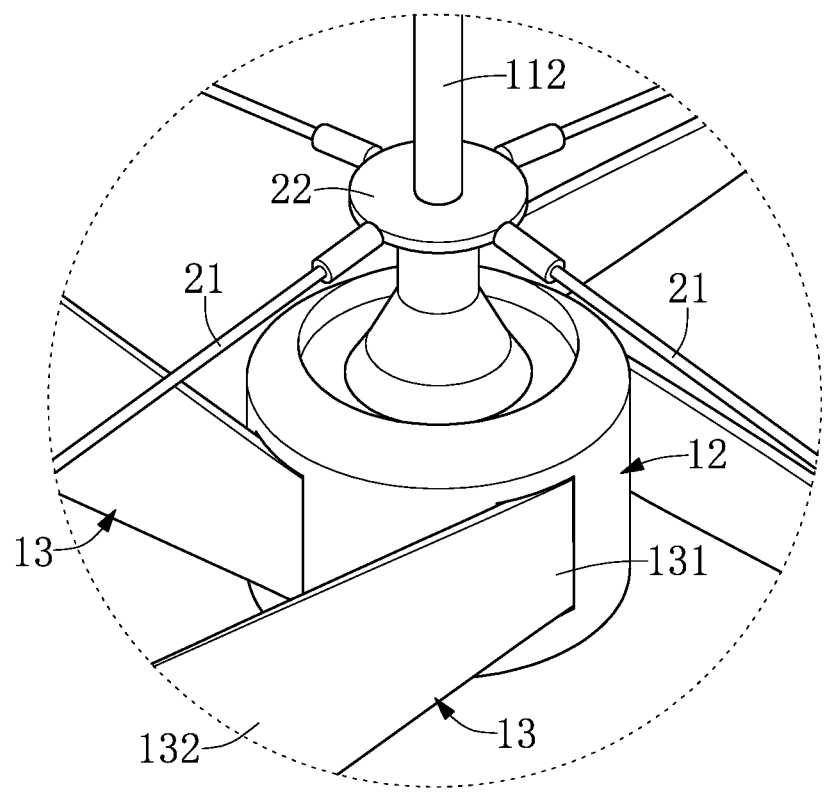
FIG. 4 is an enlarged view of part IV of FIG. 1.

As shown in FIG. 1, FIG. 2, and FIG. 4, in the present embodiment, the ceiling fan blades 13 are substantially rectangular, and each of the ceiling fan blades 13 has a mounting portion 131, a fan main body 132 connected to the mounting portion 131, and a fan end 133 formed on the fan main body 132 and being distant from the mounting portion 131. In other words, each of the ceiling fans 13 has an end that is distant from the motor 12, and the end is defined as the fan end 133.

It should be noted that the mounting portion 131 is configured to be mounted in the motor housing. A quantity of the ceiling fan blades 13 is preferably four, and the ceiling fan blades 13 and the motor 12 can together be a 52 inches ceiling fan in the present embodiment, but is not limited thereto. For instance, in other embodiments not shown in the present disclosure, the quantity of the ceiling fan blades 13, a size of the ceiling fan blades 13, and a size of the motor 12 can be adjusted according to practical requirements.

Figure 5:
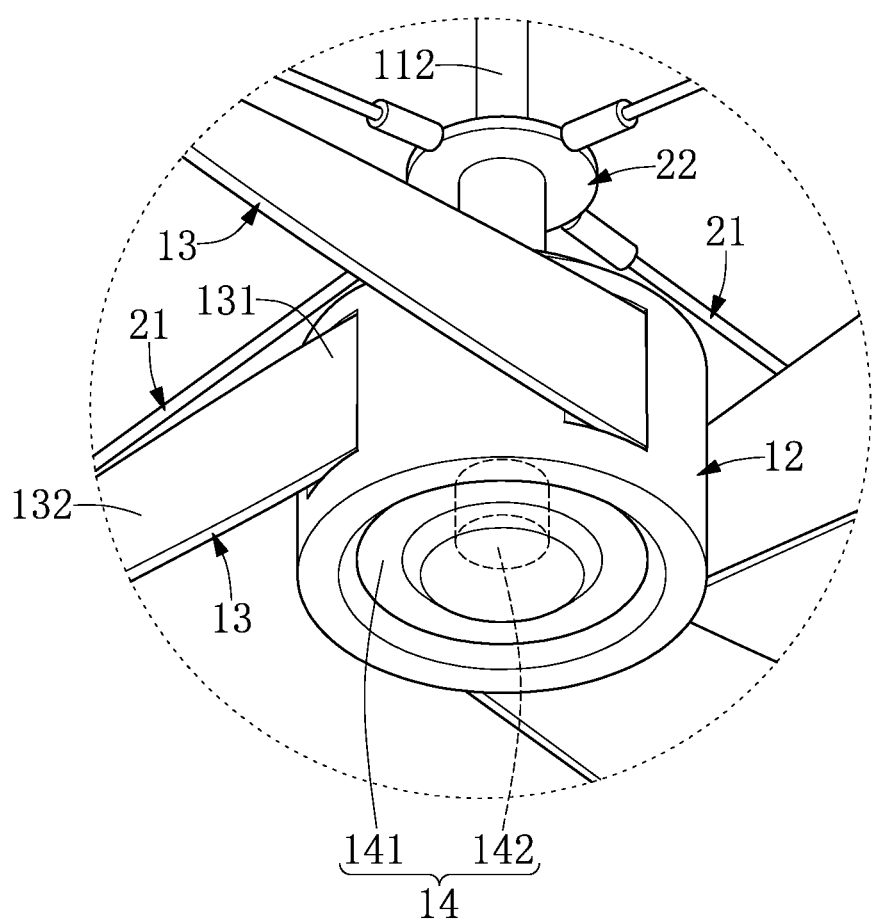
FIG. 5 is an enlarged view of part V of FIG. 2.

As shown in FIG. 2 and FIG. 5, the ceiling fan lamp 14 is in an annular shape, and the ceiling fan lamp 14 includes a lampshade 141 and at least one illuminating element 142 arranged inside the lampshade 141. Specifically, the lampshade 141 is mounted on the side of the motor 12 that is relatively far away from the main shaft 11, and the least one illuminating element 142 is an LED module, but the present disclosure is noted limited thereto. For instance, in other embodiments of the present disclosure, the least one illuminating element 142 can be a plurality of LED bulbs. It should be noted that a structural improvement of the ceiling fan lamp 14 is not the focus of the present disclosure, and will not be further described herein.

This concludes descriptions regarding the main body 1, and the bracket set 2 will be described next. As shown in FIG. 1, the bracket set 2 includes a plurality of brackets 21 and a plurality of first connecting members 22 connected to the brackets 21, and the first connecting members 22 can be detachably mounted on the connecting shaft 112 of the main shaft 11. Furthermore, one of the first connecting members 22 is adjacent to a connection part between the connecting shaft 112 and the motor 12.

Specifically, in the present embodiment, the first connecting members 22 are substantially in an annular shape, and are spaced apart from each other on the connecting shaft 112. A quantity of the first connecting members 22 is two, and a quantity of the brackets 21 is eight. Four of the brackets 21 each have an end that is connected to one of the first connecting members 22, and another four of the brackets 21 each have one end that is connected to another one of the first connecting members 22. Accordingly, the eight brackets 21 can be connected to the main shaft 11 through the two first connecting members 22.

It should be noted that the quantity of the first connecting members 22 and that of the brackets 21 can be adjusted according to practical requirements, and a structure of each of the first connecting members 22 is substantially the same, but the present disclosure is not limited thereto. For instance, in other embodiments not shown in the present disclosure, the quantity of the brackets 21 can be six, and the structure of each of the first connecting members 22 can be different.

This concludes descriptions regarding the bracket set 2, and the surrounding device 3 will be described next. As shown in FIG. 1 and FIG. 2, the surrounding device 3 has a three-dimensional circular shape in the present embodiment. In addition, the surrounding device 3 includes a plurality of surrounding portions 31 assembled to each other, a spoiler structure 32 formed on the surrounding portions 31, at least one functional component 33 disposed on insides of the surrounding portions 31, and a plurality of second connecting members 34 disposed on the surrounding portions 31, but the present disclosure is not limited thereto. For instance, in other embodiments not shown in the present disclosure, the surrounding device 3 can be provided without the spoiler structure 32 and the at least one functional component 33.

It should be noted that for ease of illustration, the surrounding portions 31, the spoiler structure 32, the second connecting members 34, and the at least one functional component 33 are sequentially described. The connection relationships of the surrounding portions 31, the spoiler structure 32, the second connecting members 34, and the at least one functional component 33 will be described in due course.

As shown in FIG. 1 and FIG. 2, a quantity of the surrounding portions 31 is four, and the four surrounding portions 31 are configured to assemble to each other, so as to correspondingly form the surrounding device 3 in the three-dimensional circular shape. However, the present disclosure is not limited thereto. For instance, in other embodiments not shown in the present disclosure, the quantity of the surrounding portions 31 can be adjusted according to practical requirements.

This concludes descriptions regarding the surrounding portions 31, and the spoiler structure 32 will be described next. As shown in FIG. 1 and FIG. 6 to FIG. 8, the surrounding device 3 has the spoiler structure 32 formed on a side thereof, the side of the surrounding device 3 is relatively adjacent to the ceiling fan blades 13, and the spoiler structure 32 can be used to guide the air to flow through the surrounding device 3. In other words, the spoiler structure 32 is formed on a side of each of the surrounding portions 31, and the side of each of the surrounding portions 31 is relatively adjacent to the ceiling fan blades 13.

Figure 6:
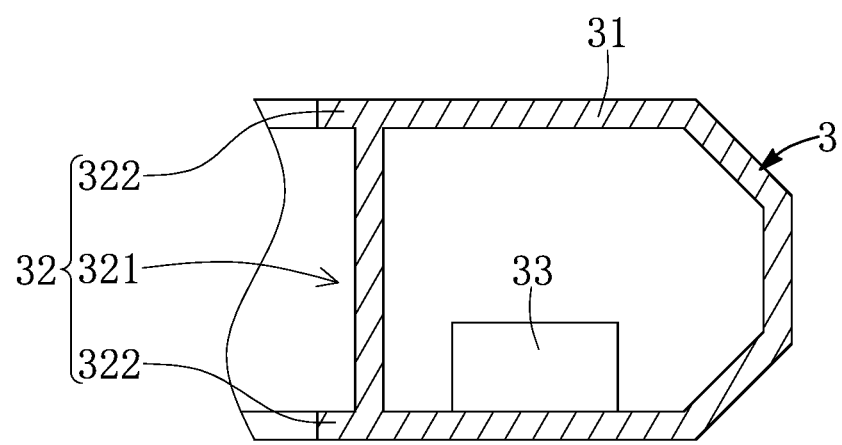
FIG. 6 is a cross-sectional view taken along line IX-IX of FIG. 1.
Figure 7:
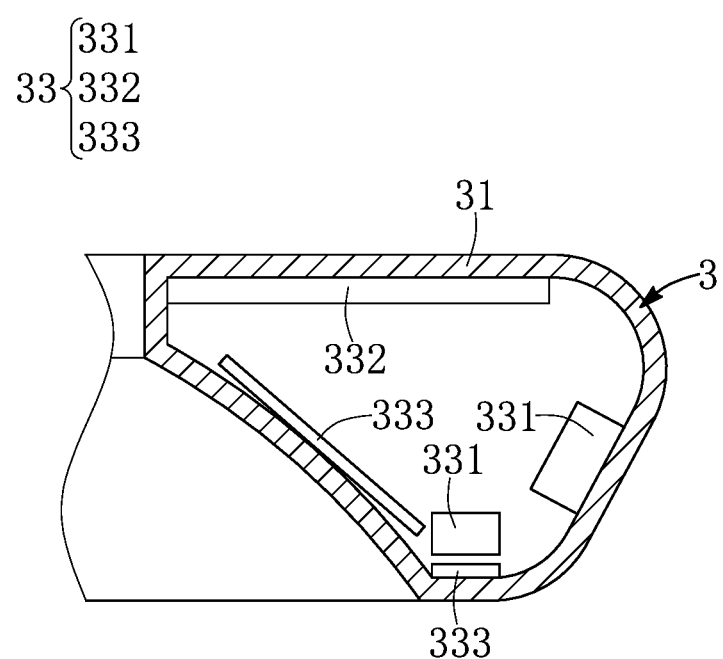
FIG. 7 is another cross-sectional view taken along line IX-IX of FIG. 1.

Specifically, as shown in FIG. 6 and FIG. 7, the spoiler structure 32 in the present embodiment is a groove, and the spoiler structure 32 has a groove bottom 321 and two groove sidewalls 322 connected to the groove bottom 321, but the present disclosure is not limited thereto. For instance, in other embodiments not shown in the present disclosure, a quantity of the groove sidewall 322 in the spoiler structure 32 can be one. Or, as shown in FIG. 7, the spoiler structure 32 can be in an arc shape, an inside of the surrounding device 3 has at least four inner sides (not labeled), and one of the inner sides corresponds in position to the spoiler structure 32. The at least four inner sides are configured to have the at least four of the functional component 33 disposed thereon.

This concludes descriptions regarding the spoiler structure 32, and the second connecting members 34 will be described next. As shown in FIG. 1 and FIG. 7, a quantity of the second connecting members 34 is four, and the four second connecting members 34 are respectively disposed on the four surrounding portions 31, but the present disclosure is not limited thereto. For instance, in other embodiments not shown in the present disclosure, the quantity of the second connecting members 34 can be adjusted according to practical requirements.

Specifically, each of the second connecting members 34 is partly disposed inside a corresponding one of the surrounding portions 31, and each of the second connecting members 34 is connected to two of the brackets 21. Furthermore, two ends of said two brackets 21 are respectively connected to the two first connecting members 22, and the two ends are far away from the second connecting members 34.

This concludes descriptions regarding the second connecting members 34, and the at least one functional component 33 will be described next. The functional component 33 is configured to disinfect or sterilize air or to provide lighting. As shown in FIG. 1 and FIG. 2, each of the functional components 33 in the present embodiment is an LED ultraviolet lamp, and is configured to emit an ultraviolet light with a wavelength between 200 nm and 280 nm, but the present disclosure is not limited thereto. For instance, in other embodiments of the present disclosure, each of the functional components 33 can also be an ozone generator that is configured to generate ozone with a flow rate between 2 mg/hr and 8 mg/hr.

Accordingly, by virtue of "the at least one functional component 33 being configured to generate ozone with the flow rate between 2 mg/hr and 8 mg/hr", the air flowing through the spoiler structure 32 can be disinfected and sterilized by the at least one functional component 33, so that an accumulated ozone concentration in an indoor space where the ceiling fan 100 is installed is between 0.03 ppm and 0.08 ppm within four hours.

As shown in FIG. 6, it should be noted that each of the functional components 33 is disposed on a bottom surface inside any one of the surrounding portions 31, but the present disclosure is not limited thereto. For instance, as shown in FIG. 7, a cross-section of any one of the surrounding portions 31 is fan-shaped, and any one of the surrounding portions 31 can be provided without the spoiler structure 32 in other embodiments of the present disclosure. The at least one functional component 33 can be disposed on the bottom surface of any one of the surrounding portions 31, two side surfaces adjacent to the bottom surface, and a top surface corresponding in position to the bottom surface.

Specifically, as shown in FIG. 7, a quantity of the functional component 33 is five, and any one of the functional component 33 can be further defined as a first functional component 331, a second functional component 332, or a third functional component 333. More specifically, the first functional component 331, the second functional component 332, and the third functional component 333 can be any one of an LED ultraviolet lamp, an ozone generator, and a light-emitting diode tube (LED scene lamp). The first functional component 331 is preferably the ozone generator, the second functional component 332 is preferably the LED ultraviolet lamp, and the third functional component 333 is preferably the LED ambient light.

As shown in FIG. 7, the second functional component 332 is disposed on the top surface inside any one of the surrounding portions 31, two of the third functional components 333 are respectively disposed on the bottom surface and the side surface inside any one of the surrounding portions 31, and two of the first functional components 331 are respectively disposed on the bottom surface inside any one of the surrounding portions 31 and one of the third functional components 333 that is disposed on the bottom surface inside any one of the surrounding portions 31.

It should be noted that total quantities and respective functions of the first functional component 331, the second functional component 332, and the third functional component 333 can be adjusted according to practical requirements, and are not limited thereto.

This concludes descriptions regarding each of the components of the surrounding device 3. Next, the relative positional relationship and the connection relationship of the various components of the surrounding device 3 and other components of the ceiling fan 100 will be described. As shown in FIG. 1, the surrounding device 3 is connected to one end of each of the brackets 21 that is relatively far away from the main shaft 11. Further, the surrounding device 3 is around and is spaced apart from an end (that is, the fan end 133) of each of the ceiling fan blades 13, and the end of each of the ceiling fan blades 13 is relatively far away from the motor 12.

Beneficial Effects of the Embodiments

In conclusion, in the ceiling fan 100 and the surrounding device 3 provided by the present disclosure, by virtue of "the surrounding device 3 including at least one functional component 33 configured to disinfect or sterilize air or to provide lighting", the ceiling fan 100 of the present disclosure can be used to disinfect or sterilize air or to provide lighting, and the ceiling fan 100 can have a much larger sterilization area than a ceiling fan having a sterilization device that is disposed on a motor or a ceiling tube thereof. Taking a 52 inches ceiling fan as an example, the diameter of a motor contained therein is about 20 cm, so that a sterilization area of a sterilization device provided on the motor will be limited to 1256 cm². However, by mounting the at least one functional component 33 on the 52 inches ceiling fan, a sterilization area of the at least one functional component 33 will be enlarged by virtue of the overall area of the 52 inches ceiling fan with 132 cm spiral diameter.

Specifically, by virtue of "the at least one functional component 33 being configured to emit an ultraviolet light with a wavelength between 200 nm and 280 nm", the air flowing through the spoiler structure 32 can be disinfected and sterilized through the at least one functional component 33.

Specifically, by virtue of "the at least one functional component 33 being configured to generate ozone with a flow rate between 2 mg/hr and 8 mg/hr", the air flowing through the spoiler structure 32 can be disinfected and sterilized through the at least one functional component 33, so that the accumulated ozone concentration in an indoor space where the ceiling fan 100 is installed is between 0.03 ppm and 0.08 ppm within four hours.

Specifically, by virtue of "the spoiler structure 32 being a groove, and the spoiler structure 32 having the groove bottom 321 and the two groove sidewalls 322 connected to the groove bottom 321", the air guiding effect of the spoiler structure 32 can be further improved.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A ceiling fan, comprising:
a main body including a main shaft, a motor connected to the main shaft, and a plurality of ceiling fan blades connected to the motor;
a bracket set including a plurality of brackets, wherein each of the brackets has one end connected to the main shaft; and
a surrounding device connected to another end of each of the brackets, wherein another end of each of the brackets is relatively far away from the main shaft, the surrounding device is roundly arranged around and spaced apart from an end of each of the ceiling fan blades, and the end of each of the ceiling fan blades is distant from the motor, and wherein the surrounding device includes at least one functional component that is configured to disinfect or sterilize air or to provide lighting;
wherein the surrounding device further includes:
a plurality of surrounding portions and a spoiler structure, wherein the surrounding portions are configured to assemble to each other, so as to correspondingly form the surrounding device having an annular shape and defining a closed space within, wherein the surrounding device has a top surface and a bottom surface, and a cross section of the surrounding device is getting thinner from the top surface to the bottom surface of the surrounding device, wherein the spoiler structure is formed on a side surface of each of the surrounding portions;
wherein the at least one functional component is disposed in the closed space.

2. The ceiling fan according to claim 1, wherein the surrounding device has a spoiler structure is formed on a side thereof, the side of the surrounding device is adjacent to the ceiling fan blades, and the spoiler structure is configured to guide the air to flow through the surrounding device.

3. The ceiling fan according to claim 2, wherein the spoiler structure is in an arc shape, an inside of the surrounding device has at least four inner sides, and one of the inner sides corresponds in position to the spoiler structure, and wherein the at least four inner sides are configured to have at least four of the functional component disposed thereon.

4. The ceiling fan according to claim 1, wherein the at least one functional component is disposed on an inside of the surrounding device, and the at least one functional component is configured to emit an ultraviolet light with a wavelength between 200 nm and 280 nm.

5. The ceiling fan according to claim 1, wherein the at least one functional component is disposed on an inside of the surrounding device, and the at least one functional component is configured to generate ozone with a flow rate between 2 mg/hr and 8 mg/hr.

6. The ceiling fan according to claim 1, wherein the at least one functional component is disposed on an inside of the surrounding device, and the at least one functional component is a light emitting diode tube and is configured to provide lighting.

7. The ceiling fan according to claim 1, wherein the spoiler structure is a groove, and the spoiler structure has a groove bottom and two groove sidewalls connected to the groove bottom.

8. A surrounding device configured to be roundly arranged around and spaced apart from an end of each of a plurality of ceiling fan blades of a ceiling fan, the surrounding device comprising:
a plurality of surrounding portions and a spoiler structure, wherein the surrounding portions are configured to assemble to each other, so as to correspondingly form the surrounding device having an annular shape and defining a closed space within, wherein the surrounding device has a top surface and a bottom surface, and a cross section of the surrounding device is getting thinner from the top surface to the bottom surface of the surrounding device, wherein the spoiler structure is formed on a side surface of each of the surrounding portions, and is configured to guide the air to flow through the surrounding device; and at least one functional component disposed in the closed space, wherein the at least one functional component is configured to disinfect or sterilize air or to provide lighting.

9. The surrounding device according to claim 8, wherein the least one functional components is an ultraviolet lamp tube and is configured to emit an ultraviolet light with a wavelength between 200 nm and 280 nm.

* * * * *